US012671001B2

(12) United States Patent (10) Patent No.: US 12,671,001 B2
Mink et al. (45) Date of Patent: Jun. 30, 2026

(54) TELEHEALTH SERVICE DELIVERY SYSTEM

(71) Applicants: Kelly Mink, Corinth, KY (US); Benjamin Mink, Pleasant Plain, OH (US)

(72) Inventors: Kelly Mink, Corinth, KY (US); Benjamin Mink, Pleasant Plain, OH (US)

( * ) Notice: Subject to any disclaimer, the term of this patent is extended or adjusted under 35 U.S.C. 154(b) by 303 days.

(21) Appl. No.: 17/724,156

(22) Filed: Apr. 19, 2022

(65) Prior Publication Data

US 2022/0238240 A1 Jul. 28, 2022

Related U.S. Application Data

(63) Continuation-in-part of application No. 15/184,208, filed on Jun. 16, 2016, now abandoned.

(51) Int. Cl.
  *G16H 80/00* (2018.01)
  *G16H 10/60* (2018.01)
  *G16H 20/10* (2018.01)
(52) U.S. Cl.
  CPC ............. *G16H 80/00* (2018.01); *G16H 10/60* (2018.01); *G16H 20/10* (2018.01)

(58) Field of Classification Search
  CPC ......... G16H 80/00; G16H 10/60; G16H 20/10
  See application file for complete search history.

(56) References Cited

U.S. PATENT DOCUMENTS

| | | | | |
|---|---|---|---|---|
| 6,039,688 | A * | 3/2000 | Douglas | A61B 5/4866 600/300 |
| 10,430,552 | B2 * | 10/2019 | Mihai | G16H 40/67 |
| 2008/0065414 | A1 * | 3/2008 | Schoenberg | G16H 10/20 705/2 |
| 2021/0330189 | A1 * | 10/2021 | Rose | H04N 23/51 |

FOREIGN PATENT DOCUMENTS

WO WO-2012112695 A1 * 8/2012 ..... G06Q 10/063112

* cited by examiner

*Primary Examiner* — Sheetal R Paulson
(74) *Attorney, Agent, or Firm* — York Law LLC; Olen L. York, III

(57) ABSTRACT

A telehealth delivery system includes a web portal that also includes a plurality of interfaces for facilitating a synchronous patient health evaluation session via an online connection. The synchronous patient health evaluation session may be initiated by either the patient (or patient custodian) or one of several health care providers associated with the patient. The synchronous session allows multiple health care providers to observe, interact, and/or counsel a patient and/or patient custodian.

19 Claims, 1 Drawing Sheet

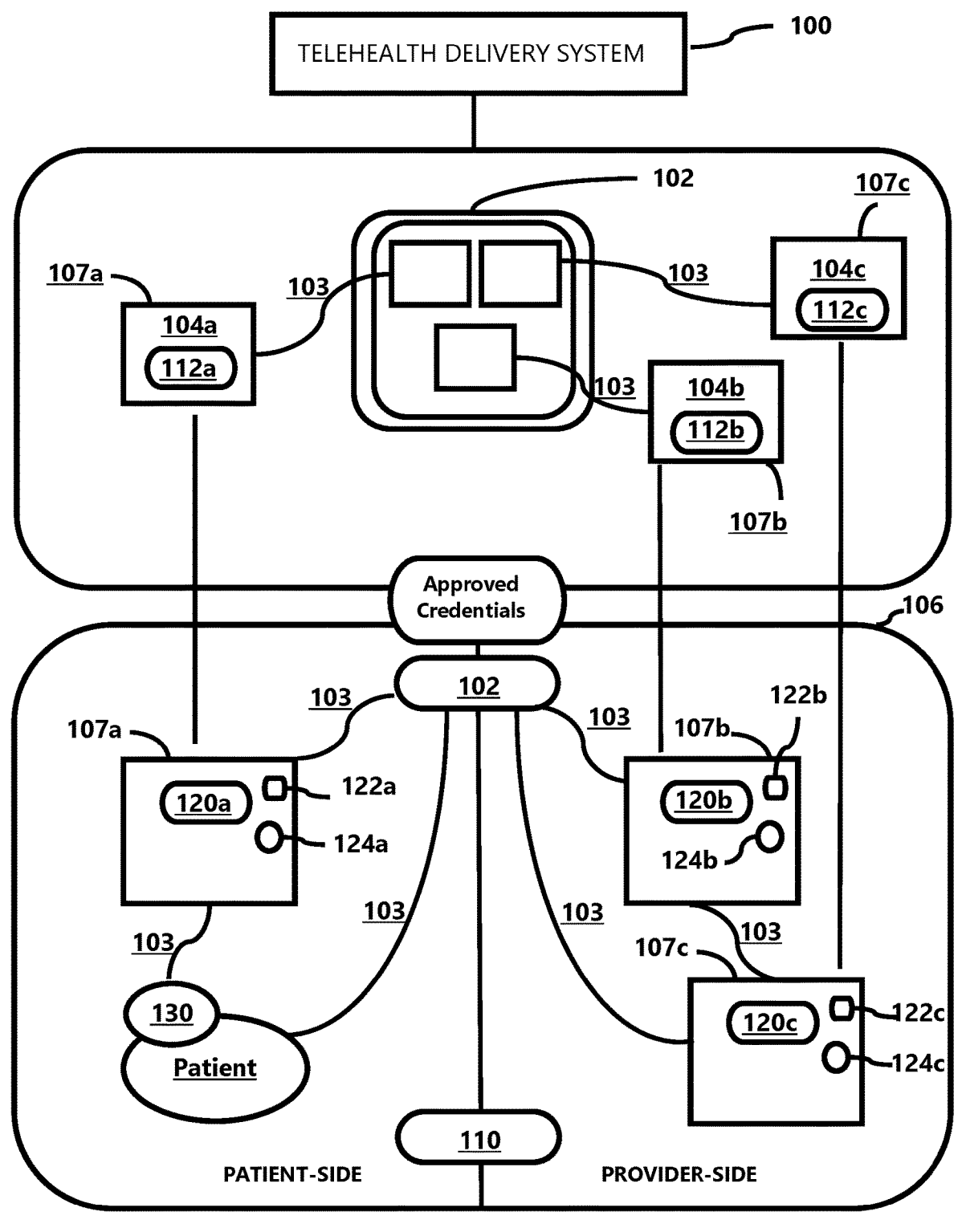

TELEHEALTH SERVICE DELIVERY SYSTEM

I. RELATED APPLICATIONS

This application is a continuation-in-part of U.S. application Ser. No. 15/184,208, filed on Jun. 16, 2016.

II. FIELD OF THE INVENTION

This application discloses claims and embodiments generally related to a telehealth delivery system, and more particularly, a telehealth delivery system for synchronous connectivity between patient and multiple health care providers.

III. BACKGROUND OF THE INVENTION

Medical services are traditionally provided to individuals at a designated health care provider facility, such as a physician's office, a physician group facility, and/or a hospital, among other variants. Typically, an individual contacts the provider when medical assistance or advice is sought. Upon request, the provider-side sets up an appointment time and date. Because of the demand for provider services, flexibility and convenience are often quickly sacrificed for immediacy. However, such scheduling often represents a poor accommodation to the patient. In addition to the inconvenience of the time and date, travel is often required (especially for rural or remotely located individuals), and wait times are unavoidable. And, because of the size and configuration of waiting rooms, transmission of infectious disease(s) is an increased concern.

For rural residents, in which distance and/or travel time to a suitable provider facility can often be at least 30 minutes and up to 2 hours. In non-emergent situations or for pre-scheduled appointments, the travel and distance often requires the patient to clear significant blocks of time. Many patients will schedule multiple appointments for a single day to best optimize time off and/or away from work or home, resulting in long, exhausting days. Depending upon the age of the patient, such extended days can have short-term effects that carry over for one or more additional days post-appointment. In emergent situations, even emergency medical service vehicles may require more time than is ideal or preferred and can exacerbate a medical condition or problem and causing resolution to be delayed.

Telehealth and/or telemedicine have been limited to videoconferencing as the most common form of synchronous consultation. Yet, telehealth enables a patient to be monitored more frequently and conveniently obviating the need for physical visitation and increasing convenience while reducing travel. Research has indicated that continued and preventative care via telehealth has a net positive impact on the reduction of physical visitations to provider facilities. Additionally, telehealth enables consultation, diagnosis, and/or treatment via providers and specialists regardless of the geographic location relative to the patient(s). This enhances the healthcare experience, increases quality of patient care, and lowers costs associated with healthcare.

Despite these improvements in telehealth and telemedicine, there remains a need for improvements to telehealth delivery systems.

IV. SUMMARY OF THE INVENTION

In one embodiment, a synchronous telehealth service delivery system comprises a web portal having a plurality of interfaces for facilitating a synchronous patient health evaluation session via an online connection, wherein at least one of the plurality of interfaces is a patient interface and accommodates accessibility by a patient and/or a patient custodian, and wherein at least one of the plurality of interfaces is a health care provider interface and accommodates accessibility by two or more health care providers, and wherein the synchronous patient health evaluation session includes a maintenance or treatment plan for the patient. The system also includes the patient interface accessible by a remote first terminal digitally interconnected with the web portal using an online connection, the patient interface having one or more log-in fields to evaluate the patient and/or patient custodian credentials before allowing patient and/or patient custodian access to the web portal, and after patient and/or patient custodian credentials are approved the patient interface launches a patient window for audio/video transmission utilizing an associated camera and microphone. The system also includes the health care provider interface accessible by a remote second terminal digitally interconnected with the web portal using an online connection, the health care provider interface having one or more log-in fields to evaluate the first health care provider credentials and the second health care provider credentials before allowing the first health care provider and the second health care provider access to the web portal, and after the first health care provider and the second health care provider credentials are approved the health care provider interface launches at least one health care provider window for audio/visual transmission utilizing associated camera(s) and microphone(s). The system also includes the patient window and the at least one health care provider window enabling audio/video transmission between the patient and the plurality of health care providers through the web portal, wherein the web portal displays multiple video windows across multiple remote terminals accessed by the patient and/or patient custodian and the plurality of health care providers, wherein each separate remote terminal comprises a two-way camera transmission for sending and receiving video signals with at least one microphone and at least one audio speaker for sending and receiving audio signals. The system also includes one or more remote patient monitoring instruments configured for use with the patient to provide synchronous audible and/or visual biotelemetry information to the health care providers enabling synchronous medical advice from the health care providers to the patient and/or patient custodian, the one or more remote patient monitoring instruments operably coupled and in communication through the web portal via the online interconnectivity.

In another embodiment, a synchronous telehealth service delivery system comprises a web portal having a plurality of interfaces for facilitating a synchronous patient health evaluation session via an online connection, wherein at least one of the plurality of interfaces is a patient interface and accommodates accessibility by a patient and/or a patient custodian, and wherein at least one of the plurality of interfaces is a health care provider interface and accommodates accessibility by two or more health care providers, and wherein the synchronous patient health evaluation session includes a coordinated maintenance or treatment plan for the patient developed by the plurality of health care providers. The system also includes the patient interface accessible by a remote first terminal digitally interconnected with the web portal using an online connection, the patient interface having one or more log-in fields to evaluate the patient and/or patient custodian credentials before allowing patient and/or patient custodian access to the web portal, and after patient and/or patient custodian credentials are approved the patient interface launches a patient window for audio/video transmission utilizing an associated camera and microphone. The system also includes the health care provider interface accessible by a separate remote second terminal and a separate remote third terminal, the second terminal and the third terminal digitally interconnected with the web portal using an online connection, the health care provider interface having one or more log-in fields to evaluate the first health care provider credentials and the second health care provider credentials before allowing the first health care provider and the second health care provider access to the web portal, and after the first health care provider and the second health care provider credentials are approved the health care provider interface launches a first health care provider window and a separate second health care provider window, the first health care provider window and the second health care provider window providing audio/visual transmission utilizing associated camera(s) and microphone (s). The system also includes the patient window and the at least one health care provider window enabling audio/video transmission between the patient and the plurality of health care providers through the web portal, wherein the web portal displays multiple video windows across multiple remote terminals accessed by the patient and/or patient custodian and the plurality of health care providers, wherein each separate remote terminal comprises a two-way camera transmission for sending and receiving video signals with at least one microphone and at least one audio speaker for sending and receiving audio signals. The system also includes one or more remote patient monitoring instruments configured for use with the patient to provide synchronous audible and/or visual biotelemetry information to the health care providers enabling synchronous medical advice from the health care providers to the patient and/or patient custodian, the one or more remote patient monitoring instruments operably coupled and in communication through the web portal via the online interconnectivity.

V. BRIEF DESCRIPTION OF THE DRAWING(S)

The advantages and features of the invention and the respective embodiments will become better understood with reference to the following more detailed description and claims taken in conjunction with the accompanying drawings, in which like elements are identified with like symbols, and in which:

FIG. 1 is a schematic of the system 100 described and disclosed that provides a synchronous patient evaluation session 106.

VI. DETAILED DESCRIPTION OF THE EMBODIMENT(S)

It will be readily understood that the components of the present invention, as generally described and illustrated in the figures herein, may be arranged and designed in a wide variety of different configurations. Thus, the following detailed description of the embodiments, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

Consistent with the illustration in FIG. 1, included herewith, a telehealth delivery system 100 comprising a web portal 102 having a plurality of interfaces 104 for facilitating a synchronous patient health evaluation session 106 via an online connection 103 is described herein. The synchronous patient health evaluation session 106 may be initiated by either the patient (or patient custodian) or one of several health care providers associated with the patient and/or invited for temporary or limited association as initiated by one of the several health care providers associated with the patient.

Within the system 100, at least one of the plurality of interfaces 104 is a patient interface 104a and accommodates accessibility by a patient and/or a patient custodian, and wherein at least one of the plurality of interfaces 104 is a health care provider interface 104b. In one embodiment, the patient interface 104a includes a remote first terminal 107a and the health care provider interface 104b accommodates accessibility by two or more health care providers via a single remote second terminal 107b. In another embodiment, the patient interface 104a incudes a remote first terminal 107a and the health care provider interface 104b accommodates accessibility by two or more health care providers via a remote second terminal 107b and a remote third terminal 107c. In either embodiment, the synchronous patient health evaluation session 106 includes a coordinated maintenance or treatment plan 110 for the patient developed by the plurality of health care providers interconnected via the web portal 102. It is envisioned that as part of the plan 110 is the inclusion of the transmission of electronic dispensing of a prescription request(s) to an identified pharmacy via the web portal 102.

The patient interface 104a accessible by the remote first terminal 107a digitally interconnected with the web portal 102 using an online connection 103, the patient interface 104a comprises one or more log-in fields 112a to evaluate the patient and/or patient custodian credentials before allowing patient and/or patient custodian access to the web portal 102. If and after patient and/or patient custodian credentials are approved the patient interface 104a launches a patient window 120a for audio/video transmission utilizing an associated camera 122a and microphone 124a.

For either of the embodiments described above concerning the health care provider interface 104b, the interface 104b comprises one or more log-in fields 112b to evaluate the first health care provider credentials and the second health care provider credentials before allowing the first health care provider and the second health care provider access to the web portal 102. If and after the first health care provider and the second health care provider credentials are approved the health care provider interface 104b launches a first health care provider window 120b and a separate second health care provider window 120c, the first health care provider window and the second health care provider window 120b, 120c providing audio/visual transmission utilizing associated camera(s) 122b, 122c and microphone (s) 124b, 124c.

The credentialing of the patient (or patient custodian) and the one or more health care providers provides the requisite security and privacy necessary to conduct a telehealth session without fear of disclosure, broadcast, and/or dissemination. In particular, it is envisioned that the credentialing of each entryway into the system 100 (via the patient-side and the health care provider-side) is consistent and in compliance with HIPAA. Via HIPAA compliance, confidence and integrity in the system 100 will be improved. HIPAA compliance also promotes secure preservation of electronic health records (EHR) and electronic medical records (EMR) as well as all such records and entries related to such records, data, and information. Initiation of the session 106 by the patient and/or patient custodian may include prompts for patient and/or patient custodian to update patient information, including non-health information and health-related information.

The patient window 120a and the at least one health care provider window 120b (and/or 120c) enable audio/video transmission between the patient and the plurality of health care providers through the web portal 102. The web portal 102 displays multiple video windows across multiple remote terminals accessed by the patient and/or patient custodian and the plurality of health care providers. Each separate remote terminal 107a, 107b, 107c comprises a two-way camera transmission for sending and receiving video signals with at least one microphone and at least one audio speaker for sending and receiving audio signals. It is envisioned that each separate remote terminal 107a, 107b, 107c may comprise one or combinations of a PC terminal, a laptop terminal, a smartphone, a smartwatch, a tablet, a television, and/or other similar technology that enables a user or users to remotely access the web portal 102.

The system 100 may include one or more remote patient monitoring instruments 130 configured for use with the patient to provide synchronous audible and/or visual biotelemtry information to the health care providers and enabling synchronous medical advice from the health care providers to the patient and/or patient custodian. The one or more remote patient monitoring instruments 130 are operably coupled and in communication through the web portal via the online interconnectivity.

It is envisioned that the one or more remote patient monitoring instruments (devices) 130 may include the following instruments and/or devices used for monitoring vital signs and/or chronic illness/disease. More particularly, vital sign remote patient monitoring instruments (devices) 130 may include such devices utilized for collecting data for blood pressure, glucose levels (e.g., glucometer), pulse oxygen data (e.g., pulse oximeter), cardio data (e.g., ECG, stethoscope), body temperature and/or body weight, as well as such devices for monitoring and controlling insulin levels and other chronic disease or illness. It is envisioned that these instruments 130 may be single-data instruments, multi-data instruments, wearable devices (e.g., wearables), and/or a combination of these items.

It is envisioned that the synchronous patient health evaluation session 106 may include advertising and/or promotion. In one embodiment, the advertisement/promotion may be included at the initiation of the session 106. In another embodiment, the advertisement/promotion may be included at the conclusion of the session 106. In another embodiment, the advertisement/promotion may be included at the initiation and conclusion of the session 106. The advertisement/promotion may assume a variety of forms, including a fixed image, fixed image with voiceover, video, video with voiceover, and/or a combination thereof.

It is also envisioned that the system 100 may be utilized in delivery of a number of telehealth services, including general health maintenance, annual exams, and/or specialized medical services. For example, including but limited to the following specialized medical services and/or areas of concern, the system 100 may include cardiology, dentistry, dermatology, endocrinology, gastroenterology, genetics, gerontology, gyneology, hematology, hepatology, immunology, infectious disease, internal medicine, nephrology, neurology, obstetrics, oncology, ophthalmology, orthopedics, otolaryngology, pallitative medicine, pathology, pediatrics, podiatry, psychiatry, pulmonology, radiology, rheumatology, serology, toxicology, urology, general and specific surgical cases, and emergency and/or disaster medicine. Other umbrella services, including athletic training and/or sports medicine, aviation, family medicine, intensive care, military medicine, rehabilitation services, rural medicine, space medicine, transplantation medicine, tropical medicine, and/or wilderness medicine, may be encompassed by the system 100.

It is envisioned that specific health care and/or medical services may be delivered through the telehealth system 100 described above. For example, these services may include providing advice and/or recommendations related to an existing or a new medical condition, diagnosing and/or treating an existing or a new medical condition, providing immediate or concurrent referral service(s) based on an existing or new medical condition, prescribing medication or other treatment measures, periodic medical monitoring of one or more existing medical condition(s), providing follow-up monitoring and/or routine examination(s) and/or check-ups, mental health counseling and/or referral, providing general health or health-related information, and/or wellness information and/or counseling.

It is envisioned that the system 100 may include entry and/or verification of credentials utilizing a variety of personal information related to the patient. For example, including but not limited to, patient name, address, contact information (e.g., cell or phone number, email address), age, gender, height, weight, medical history, current medicine(s), insurance information, medical power of attorney, allergy information, general or specific health or medical records, and/or pharmacy information. Additional information that may be used (but not necessarily required) to initiate a telehealth system 100 synchronous patient health evaluation session 106 may include request for session, patient symptom(s), specific health care request(s), and/or other related information.

It is to be understood that the embodiments and claims are not limited in its application to the details of construction and arrangement of the components set forth in the description and illustrated in the drawings. Rather, the description and the drawings provide examples of the embodiments envisioned, but the claims are limited to the specific embodiments. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the U.S. Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. A synchronous telehealth service delivery system comprising:

a web portal having a plurality of interfaces for facilitating a synchronous patient health evaluation session via an online connection, wherein at least one of the plurality of interfaces is a patient interface and accommodates accessibility by a patient and/or a patient custodian, and wherein at least one of the plurality of interfaces is a health care provider interface and accommodates accessibility by two or more health care providers, and wherein the synchronous patient health evaluation session includes a maintenance or treatment plan for the patient;

the patient interface accessible by a remote first terminal digitally interconnected with the web portal using an online connection, the patient interface having one or more log-in fields to evaluate the patient and/or patient custodian credentials before allowing patient and/or patient custodian access to the web portal, and after patient and/or patient custodian credentials are approved the patient interface launches a patient window for audio/video transmission utilizing an associated camera and microphone;

the health care provider interface accessible by a remote second terminal digitally interconnected with the web portal using an online connection, the health care provider interface having one or more log-in fields to evaluate the first health care provider credentials and the second health care provider credentials before allowing the first health care provider and the second health care provider access to the web portal, and after the first health care provider and the second health care provider credentials are approved the health care provider interface launches at least one health care provider window for audio/visual transmission utilizing associated camera(s) and microphone(s);

the patient window and the at least one health care provider window enabling audio/video transmission between the patient and the plurality of health care providers through the web portal, wherein the web portal displays multiple video windows across multiple remote terminals accessed by the patient and/or patient custodian and the plurality of health care providers, wherein each separate remote terminal comprises a two-way camera transmission for sending and receiving video signals with at least one microphone and at least one audio speaker for sending and receiving audio signals; and, one or more remote patient monitoring instruments configured for use with the patient to provide synchronous audible and/or visual biotelemetry information to the health care providers enabling synchronous medical advice from the health care providers to the patient and/or patient custodian, the one or more remote patient monitoring instruments operably coupled and in communication through the web portal via the online interconnectivity.

2. The system of claim 1, wherein the synchronous patient health care evaluation session is initiated by the patient and/or patient custodian.

3. The system of claim 1, wherein the synchronous patient health care evaluation session is initiated by one of the health care providers.

4. The system of claim 1, wherein the synchronous patient health care evaluation session includes transmission of electronic dispensing of a prescription request(s) to an identified pharmacy via the web portal.

5. The system of claim 1, wherein the synchronous patient health care evaluation session includes preserving the electronic medical records (EMR) and the electronic health records (EHR) associated with the patient via the web portal.

6. The system of claim 1, wherein the synchronous patient health care evaluation session includes advertising during the session.

7. The system of claim 1, wherein the synchronous patient health care evaluation session includes HIPAA compliance verification.

8. The system of claim 1, wherein the synchronous patient health care evaluation session includes prompts for patient and/or patient custodian to update patient information, including non-health information and health-related information.

9. The system of claim 1, wherein the synchronous patient health care evaluation session includes establishing the session via computer, smartphone, tablet, or other similar device.

10. A synchronous telehealth service delivery system comprising:

a web portal having a plurality of interfaces for facilitating a synchronous patient health evaluation session via an online connection, wherein at least one of the plurality of interfaces is a patient interface and accommodates accessibility by a patient and/or a patient custodian, and wherein at least one of the plurality of interfaces is a health care provider interface and accommodates accessibility by two or more health care providers, and wherein the synchronous patient health evaluation session includes a coordinated maintenance or treatment plan for the patient developed by the plurality of health care providers;

the patient interface accessible by a remote first terminal digitally interconnected with the web portal using an online connection, the patient interface having one or more log-in fields to evaluate the patient and/or patient custodian credentials before allowing patient and/or patient custodian access to the web portal, and after patient and/or patient custodian credentials are approved the patient interface launches a patient window for audio/video transmission utilizing an associated camera and microphone;

the health care provider interface accessible by a separate remote second terminal and a separate remote third terminal, the second terminal and the third terminal digitally interconnected with the web portal using an online connection, the health care provider interface having one or more log-in fields to evaluate the first health care provider credentials and the second health care provider credentials before allowing the first health care provider and the second health care provider access to the web portal, and after the first health care provider and the second health care provider credentials are approved the health care provider interface launches a first health care provider window and a separate second health care provider window, the first health care provider window and the second health care provider window providing audio/visual transmission utilizing associated camera(s) and microphone(s);

the patient window and the at least one health care provider window enabling audio/video transmission between the patient and the plurality of health care providers through the web portal, wherein the web portal displays multiple video windows across multiple remote terminals accessed by the patient and/or patient custodian and the plurality of health care providers, wherein each separate remote terminal comprises a two-way camera transmission for sending and receiving video signals with at least one microphone and at least one audio speaker for sending and receiving audio signals; and, one or more remote patient monitoring instruments configured for use with the patient to provide synchronous audible and/or visual biotelemetry information to the health care providers enabling synchronous medical advice from the health care providers to the patient and/or patient custodian, the one or more remote patient monitoring instruments operably coupled and in communication through the web portal via the online interconnectivity.

11. The system of claim 10, wherein the synchronous patient health care evaluation session is initiated by the patient and/or patient custodian.

12. The system of claim 10, wherein the synchronous patient health care evaluation session is initiated by one of the health care providers.

13. The system of claim 10, wherein the synchronous patient health care evaluation session includes transmission of electronic dispensing of a prescription request(s) to an identified pharmacy via the web portal.

14. The system of claim 10, wherein the synchronous patient health care evaluation session includes preserving the electronic medical records (EMR) and the electronic health records (EHR) associated with the patient via the web portal.

15. The system of claim 10, wherein the synchronous patient health care evaluation session includes advertising during the session.

16. The system of claim 10, wherein the synchronous patient health care evaluation session includes HIPAA compliance verification.

17. The system of claim 10, wherein the synchronous patient health care evaluation session includes appropriate coding and associated billing for the patient's care.

18. The system of claim 10, wherein the synchronous patient health care evaluation session includes prompts for patient and/or patient custodian to update patient information, including non-health information and health-related information.

19. The system of claim 10, wherein the synchronous patient health care evaluation session includes establishing the session via computer, smartphone, tablet, or other similar device.

\* \* \* \* \*